United States Patent [19]

Elbe et al.

[11] Patent Number: 4,748,249

[45] Date of Patent: May 31, 1988

[54] COMBATING FUNGI WITH NOVEL AZOLYL-TETRAHYDROFURAN-2-YLIDENE-METHANES

[75] Inventors: Hans-Ludwig Elbe, Wuppertal; Manfred Jautelat; Karl H. Büchel, both of Burscheid; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[21] Appl. No.: 879,661

[22] Filed: Jun. 27, 1986

Related U.S. Application Data

[62] Division of Ser. No. 658,941, Oct. 9, 1984, Pat. No. 4,619,940.

[30] Foreign Application Priority Data

Oct. 11, 1983 [DE] Fed. Rep. of Germany ....... 3336861

[51] Int. Cl.$^4$ ................... A01N 43/50; A01N 43/653; C07D 249/08; C07D 405/06
[52] U.S. Cl. .................................. 548/262; 548/336; 548/101; 549/504; 568/419
[58] Field of Search ................ 548/262, 336; 514/383, 514/397

[56] References Cited

U.S. PATENT DOCUMENTS

| | | | |
|---|---|---|---|
| 4,289,526 | 9/1981 | Worthington et al. | 548/262 |
| 4,312,880 | 1/1982 | Draber et al. | 548/341 |
| 4,487,776 | 12/1984 | Elbe et al. | 548/262 |
| 4,518,415 | 5/1985 | Marchington et al. | 548/262 |
| 4,547,515 | 10/1985 | Elbe et al. | 514/383 |
| 4,548,945 | 10/1985 | Holmwood et al. | 548/262 |
| 4,562,198 | 12/1985 | Elbe et al. | 514/383 |

FOREIGN PATENT DOCUMENTS

| | | | |
|---|---|---|---|
| 0054865 | 6/1982 | European Pat. Off. | 548/262 |
| 0071095 | 2/1983 | European Pat. Off. | 548/262 |

*Primary Examiner*—Glennon H. Hollrah
*Assistant Examiner*—Patricia L. Morris
*Attorney, Agent, or Firm*—Sprung Horn Kramer & Woods

[57] ABSTRACT

Azolyl-tetrahydrofuran-2-ylidene-methanes of the formula

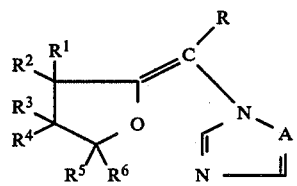

in which

A represents a nitrogen atom or the CH group,

R represents alkyl, alkenyl, alkynyl, alkoxyalkyl, alkylthioalkyl, halogenoalkyl, halogenoalkoxyalkyl, halogenoalkylthioalkyl, halogenoalkenyl, optionally substituted aralkyl, optionally substituted aryloxyalkyl, optionally substituted arylthioalkyl, optionally substituted cycloalkyl or optionally substituted cycloalkylalkyl, $R^1$ to $R^6$ are identical or different and represent hydrogen, alkyl, halogenoalkyl or halogen, up to at most 3 of the substituents representing halogen or halogenoalkyl, or $R^1$ and $R^2$, together with the carbon atom to which they are bonded, represent optionally substituted cycloalkyl, or $R^2$ and $R^3$, together with the carbon atoms to which they are bonded, represent optionally substituted cycloalkyl, or addition products thereof with acids or metal salts. Some new intermediates are also shown.

14 Claims, No Drawings

COMBATING FUNGI WITH NOVEL AZOLYL-TETRAHYDROFURAN-2-YLIDENE-METHANES

This is a division of application Ser. No. 658,941, filed Oct. 9, 1984, now U.S. Pat. No. 4,619,940.

The present invention relates to new substituted azolyltetrahydrofuran-2-ylidene-methane derivatives, a process for their preparation and their use as fungicides.

It has already been disclosed that certain azolylalkenols, such as, for example, 1-(imidazol-1-yl)- or 1-(1,2,4-triazol-1-yl)-2-phenoxy-4,4-dimethyl-1-penten-3-have good fungicidal properties (U.S. Pat. No. 4,360,528). It has also already been disclosed that disulphides, such as, for example, zinc ethylene-1,2-bisdithiocarbamidate, are good agents for combating fungal plant diseases (compare R. Wegler, "Chemie der Pflanzenschutz- und Schädlings- bekämpfungsmittel" ("Chemistry of the Plant Protection Agents and Agents for Combating Pests"), Volume 2, page 59 et seq., Springer-Verlag 1970). However, the action of these compounds is not always completely satisfactory in certain areas of indication, in particular when low amounts and concentrations are applied.

New substituted azolyl-tetrahydrofuran-2-ylidenemethane derivatives of the general formula (I)

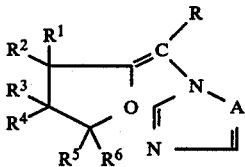

in which

A represents a nitrogen atom or the CH group,

R represents alkyl, alkenyl, alkinyl, alkoxyalkyl, alkylthioalkyl, halogenoalkyl, halogenoalkoxyalkyl, halogenoalkylthioalkyl, halogenoalkenyl, optionally substituted aralkyl, optionally substituted aryloxyalkyl, optionally substituted arylthioalkyl, optionally substituted cycloalkyl or optionally substituted cycloalkylalkyl, $R^1$ to $R^6$ are identical or different and represent hydrogen, alkyl, halogenoalkyl or halogen, up to at most 3 of the substituents representing halogen or halogenoalkyl, or $R^1$ and $R^2$, together with the carbon atom to which they are bonded, represent optionally substituted cycloalkyl, or $R^2$ and $R^3$, together with the carbon atoms to which they are bonded, represent optionally substituted cycloalkyl, and acid addition salts and metal salt complexes thereof, have been found.

The compounds of the formula (I) can be in two geometric isomer forms, depending on the arrangement of the groups bonded to the double bond; they are preferentially obtained in a varying isomer ratio. The present invention relates both to the individual isomers and to the isomer mixtures.

It has furthermore been found that the substituted azolyl-tetrahydrofuran-2-ylidene-methane derivatives of the formula (I) are obtained by a process in which azolyl-(2-hydroxytetrahydrofuran-2-yl)-methane derivatives of the formula (II)

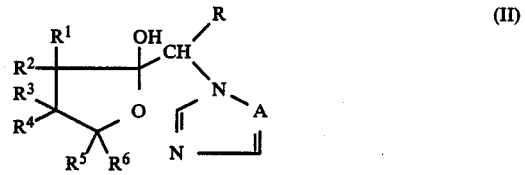

in which

A, R and $R^1$ to $R^6$ have the abovementioned meaning, are heated in the presence of a diluent and in the presence of an acid catalyst, to separate off water.

If appropriate, an acid or a metal salt can then be added onto the compounds of the formula (I) thus obtained.

It has also been found that the new substituted azolyl-tetrahydrofuran-2-ylidene-methane derivatives of the formula (I) have powerful fungicidal properties. Surprisingly, the compounds of the formula (I) according to the invention exhibit better fungicidal actions than the 1-(imidazol-1-yl)- or 1-(1,2,4-triazol-1-yl)-2-phenoxy-4,4-dimethyl-1-penten-3-ols which are substituted in the phenoxy part and are known from the prior art, and than zinc ethylene-1,2-bisdithiocarbamidate, which is also known. The active compounds according to the invention thus represent an enrichment of the art.

Formula (I) provides a general definition of the substituted azolyl-tetrahydrofuran-2-ylidene-methane derivatives according to the invention. Preferably, in this formula, A represents a nitrogen atom or the CH group;

R represents straight-chain or branched alkyl with 1 to 12 carbon atoms, or represents straight-chain or branched alkenyl or alkinyl with in each case 2 to 12 carbon atoms, or represents straight-chain or branched alkoxyalkyl or alkylthioalkyl with in each case 1 to 6 carbon atoms in each alkyl part, or represents halogenoalkyl, halogenoalkoxyalkyl or halogenoalkylthioalkyl with in each case 1 to 6 carbon atoms in each alkyl part and with in each case 1 to 6 identical or different halogen atoms, such as fluorine and chlorine atoms, or represents halogenoalkyl with 2 to 6 carbon atoms and 1 to 5 identical or different halogen atoms, such as fluorine and chlorine atoms, or represents phenylalkyl, phenoxyalkyl or phenylthioalkyl with in each case 1 to 4 carbon atoms in the alkyl part and in each case optionally monosubstituted or polysubstituted in the phenyl part by identical or different substituents, substituents which may be mentioned being: halogen; alkyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms, such as fluorine and chlorine atoms; nitro; cyano; and optionally halogen-substituted phenyl and phenoxy; or represents cycloalkyl or cycloalkylalkyl with in each case 3 to 7 carbon atoms in the cycloalkyl part and 1 to 4 carbon atoms in the alkyl part and in each case optionally monosubstituted or polysubstituted by alkyl with 1 to 4 carbon atoms;

$R^1$ to $R^6$, which can be identical or different, represent hydrogen, straight-chain or branched alkyl with 1 to 4 carbon atoms, or represent halogenoalkyl with 1 or 2 carbon atoms and 1 to 5 identical or different halogen atoms, such as fluorine and chlorine atoms, up to a maximum of 3 substituents representing halogenoalkyl, $R^3$ to $R^6$, which can be identical or different, also represent halogen, up to a maximum of 3 substituents having this meaning; or $R^1$ and $R^2$, together with the carbon atom to which they are bonded, represent cycloalkyl which has 4 to 7 carbon atoms and is optionally substituted by alkyl with 1 or 2 carbon atoms; or $R^2$ and $R^3$, together with the carbon atoms to which they are bonded, represent cycloalkyl which has 4 to 7 carbon atoms and is optionally substituted by alkyl with 1 or 2 carbon atoms.

Particularly preferred compounds of the formula (I) are those in which

A represents a nitrogen atom or the CH group;

R represents straight-chain or branched alkyl with 1 to 8 carbon atoms, or represents straight-chain or branched alkenyl or alkinyl with in each case 2 to 6 carbon atoms, or represents straight-chain or branched alkoxyalkyl or alkylthioalkyl with in each case 1 to 4 carbon atoms in each alkyl part, or represents halogenoalkyl, halogenoalkoxyalkyl or halogenoalkylthioalkyl with in each case 1 to 4 carbon atoms in each alkyl part and with in each case 1 to 5 fluorine and/or chlorine atoms, or represents halogenoalkenyl with 2 to 4 carbon atoms and 1 to 3 fluorine and/or chlorine atoms; or represents phenylalkyl, phenoxyalkyl or phenylthioalkyl with in each case 1 or 2 carbon atoms in the alkyl part and in each case optionally mono-, di- or tri-substituted in the phenyl part by identical or different substituents, substituents which may be mentioned being: fluorine, chlorine, methyl, ethyl, isopropyl, tert.-butyl, methoxy, methylthio, trifluoromethyl, trifluoromethoxy, trifluoromethylthio, nitro, cyano and optionally chlorine-substituted phenyl and phenoxy; or represents cyclohexyl or cyclohexylmethyl, in each case optionally substituted by methyl and/or ethyl;

$R^1$ to $R^6$, which can be identical or different, represent hydrogen, methyl, ethyl or halogenomethyl with 1 to 3 identical or different halogen atoms, such as fluorine and chlorine atoms, a maximum of three substituents representing halogenomethyl; or $R^3$ to $R^6$, which can be identical or different, also represent fluorine, chlorine or bromine, up to a maximum of three substituents having this meaning; or $R^1$ and $R^2$, together with the carbon atom to which they are bonded, represent cyclopentyl or cyclohexyl; or $R^2$ and $R^3$, together with the carbon atoms to which they are bonded, represent cyclopentyl or cyclohexyl.

The following compounds of the general formula (I) (wherein A represents either a nitrogen atom or the CH group) may be mentioned specifically, in addition to the compounds mentioned in the preparation examples:

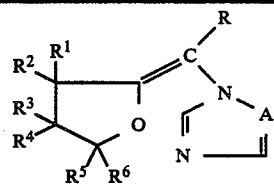

(I)

| $R^1$ | $R^2$ | $R^3$ | $R^4$ | $R^5$ | $R^6$ | R |
|---|---|---|---|---|---|---|
| CH₃ | CH₃ | H | H | H | H | 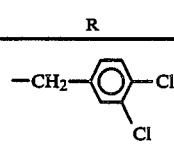 |
| CH₃ | CH₃ | H | H | H | H | 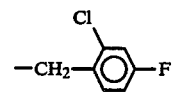 |
| CH₃ | CH₃ | H | H | H | H | 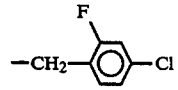 |
| CH₃ | CH₃ | H | H | H | H | 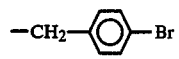 |
| CH₃ | CH₃ | H | H | H | H | 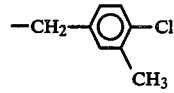 |
| CH₃ | CH₃ | H | H | H | H | 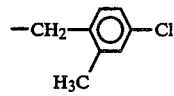 |
| CH₃ | CH₃ | H | H | H | H | 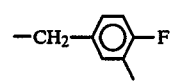 |
| CH₃ | CH₃ | H | H | H | H | 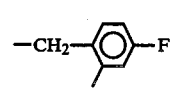 |
| CH₃ | CH₃ | H | H | H | H | 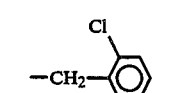 |
| CH₃ | CH₃ | H | H | H | H | 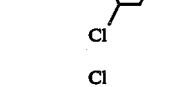 |
| CH₃ | CH₃ | H | H | H | H | 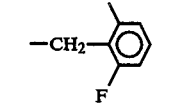 |
| CH₃ | CH₃ | H | H | H | H | 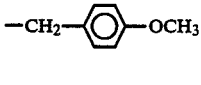 |
| CH₃ | CH₃ | H | H | H | H | 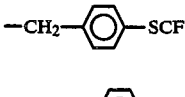 |
| CH₃ | CH₃ | H | H | H | H | 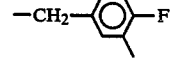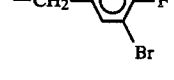 |

-continued

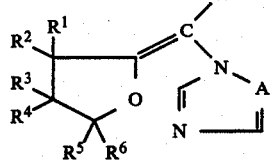

| $R^1$ | $R^2$ | $R^3$ | $R^4$ | $R^5$ | $R^6$ | R |
|---|---|---|---|---|---|---|
| CH₃ | CH₃ | H | H | H | H | —CH₂—C₆H₄—CF₃ |
| CH₃ | CH₃ | H | H | H | H | —CH₂—(2,4,5-tri-CH₃-C₆H₂) |
| CH₃ | CH₃ | H | H | H | H | —CH₂—(2,4,5-tri-Cl-C₆H₂) |
| CH₃ | CH₃ | H | H | H | H | —CH₂—C₆H₄—CH₃ |
| CH₃ | CH₃ | H | H | H | H | —CH₂—C₆H₄—CH₃ |
| CH₃ | CH₃ | H | H | H | H | —CH₂—C₆H₄—CH₃ (o-) |
| CH₃ | CH₃ | H | H | H | H | —CH₂—(2,3-di-CH₃-C₆H₃) |
| CH₃ | CH₃ | H | H | H | H | —CH₂—(2,4-di-CH₃-C₆H₃) |
| CH₃ | CH₃ | H | H | H | H | —CH₂—(3-CH₃-4-Cl-C₆H₃) |
| CH₃ | CH₃ | H | H | H | H | —CH₂—C≡CH |
| CH₃ | CH₃ | H | H | H | H | —CH₂—CH=C(Cl)—CH₃ |
| CH₃ | CH₃ | H | H | H | H | —CH₂—CH₂—CH=CH₂ |
| CH₃ | CH₃ | H | H | H | H | —CH₂—C(CH₃)=CH₃ |
| CH₃ | CH₃ | H | H | H | H | —CH₃ |
| CH₃ | CH₃ | H | H | H | H | —C₂H₅ |
| CH₃ | CH₃ | H | H | H | H | —C₃H₇—n |
| CH₃ | CH₃ | H | H | H | H | —C₅H₁₁—n |
| CH₃ | CH₃ | H | H | H | H | —C₆H₁₃—n |
| CH₃ | CH₃ | H | H | H | H | —C₇H₁₅—n |

-continued

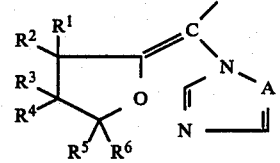

| $R^1$ | $R^2$ | $R^3$ | $R^4$ | $R^5$ | $R^6$ | R |
|---|---|---|---|---|---|---|
| CH₃ | CH₃ | H | H | H | H | —CH₂—C₆H₄—C₆H₅ |
| CH₃ | CH₃ | H | H | H | H | —CH₂—C₆H₄—C₆H₄—Cl |
| CH₃ | CH₃ | H | H | H | H | —CH₂—C₆H₄—O—C₆H₄—Cl |
| CH₃ | CH₃ | H | H | H | H | —CH(CH₃)₂ |
| CH₃ | CH₃ | H | H | H | H | —CH(CH₃)(C₂H₅) |
| CH₃ | CH₃ | H | H | H | H | —cyclopentyl |
| CH₃ | CH₃ | H | H | H | H | —CH₂—(2-F-4-CH₃-C₆H₃) |
| CH₃ | CH₃ | H | H | H | H | —CH₂—(2-Cl-4-CH₃-C₆H₃) |
| CH₃ | CH₃ | H | H | H | H | —CH₂—(2-Br-4-CH₃-C₆H₃) |
| CH₃ | CH₃ | H | H | H | H | —CH₂—C₆H₄—Cl (o-) |
| CH₃ | CH₃ | H | H | H | H | —CH₂—C₆H₄—F (o-) |
| CH₃ | CH₃ | H | H | H | H | —CH₂—cyclopentyl |
| CH₃ | CH₃ | H | H | H | H | —CH₂—O—C₆H₄—Cl |
| CH₃ | CH₃ | H | H | H | H | —CH₂—CH₂—O—C₆H₄—Cl |
| CH₃ | CH₃ | H | H | H | H | —CH₂—CH₂—C₆H₄—Cl |

-continued $$\begin{array}{c} R^2 \\ R^3 \\ R^4 \end{array} \begin{array}{c} R^1 \\ \\ O \end{array} C = C \begin{array}{c} R \\ N-A \\ \end{array} \quad (I)$$

| $R^1$ | $R^2$ | $R^3$ | $R^4$ | $R^5$ | $R^6$ | R |
|---|---|---|---|---|---|---|
| $C_2H_5$ | $CH_3$ | H | H | H | H | $-CH_2-\text{C}_6H_3(Cl)_2$ (3,4-diCl) |
| $C_2H_5$ | $CH_3$ | H | H | H | H | $-CH_2-\text{C}_6H_3(Cl)(F)$ (2-Cl, 4-F) |
| $C_2H_5$ | $CH_3$ | H | H | H | H | $-CH_2-\text{C}_6H_3(F)(Cl)$ (2-F, 4-Cl) |
| $C_2H_5$ | $CH_3$ | H | H | H | H | $-CH_2-\text{C}_6H_3(CH_3)(Cl)$ (2-CH$_3$, 4-Cl) |
| $C_2H_5$ | $CH_3$ | H | H | H | H | $-CH_2-\text{C}_6H_3(Cl)(CH_3)$ (4-Cl, 3-CH$_3$) |
| $C_2H_5$ | $CH_3$ | H | H | H | H | $-CH_2-\text{C}_6H_3(F)(CH_3)$ (4-F, 3-CH$_3$) |
| $C_2H_5$ | $CH_3$ | H | H | H | H | $-CH_2-\text{C}_6H_3(F)(CH_3)$ (4-F, 3-CH$_3$) |
| $C_2H_5$ | $CH_3$ | H | H | H | H | $-CH_2-\text{C}_6H_3(Cl)_2$ (2,6-diCl) |
| $C_2H_5$ | $CH_3$ | H | H | H | H | $-CH_2-\text{C}_6H_3(Cl)_2$ (2,6-diCl) |
| $C_2H_5$ | $CH_3$ | H | H | H | H | $-CH_2-\text{C}_6H_4Br$ (4-Br) |
| $C_2H_5$ | $CH_3$ | H | H | H | H | $-CH_2-\text{C}_6H_4OCF_3$ (4-OCF$_3$) |
| $C_2H_5$ | $CH_3$ | H | H | H | H | $-CH_2-\text{C}_6H_4SCF_3$ (4-SCF$_3$) |
| $C_2H_5$ | $CH_3$ | H | H | H | H | $-CH_2-\text{C}_6H_3(F)(Br)$ (3-F, 5-Br) |
| $C_2H_5$ | $CH_3$ | H | H | H | H | $-CH_2-\text{C}_6H_4CF_3$ (4-CF$_3$) |
| $C_2H_5$ | $CH_3$ | H | H | H | H | $-CH_2-\text{C}_6H_2(CH_3)_3$ (2,4,6-triMe) |
| $C_2H_5$ | $CH_3$ | H | H | H | H | $-CH_2-\text{C}_6H_2(Cl)_3$ (2,4,5-triCl) |
| $C_2H_5$ | $CH_3$ | H | H | H | H | $-CH_2-\text{C}_6H_4CH_3$ (4-CH$_3$) |
| $C_2H_5$ | $CH_3$ | H | H | H | H | $-CH_2-\text{C}_6H_4CH_3$ (3-CH$_3$) |
| $C_2H_5$ | $CH_3$ | H | H | H | H | $-CH_2-\text{C}_6H_4CH_3$ (2-CH$_3$) |
| $C_2H_5$ | $CH_3$ | H | H | H | H | $-CH_2-\text{C}_6H_3(CH_3)_2$ (2,3-diMe) |
| $C_2H_5$ | $CH_3$ | H | H | H | H | $-CH_2-\text{C}_6H_3(CH_3)_2$ (3,5-diMe) |
| $C_2H_5$ | $CH_3$ | H | H | H | H | $-CH_2-\text{C}_6H_3(Cl)(CF_3)$ (4-Cl, 3-CF$_3$) |
| $C_2H_5$ | $CH_3$ | H | H | H | H | $-CH_2-C\equiv CH$ |
| $C_2H_5$ | $CH_3$ | H | H | H | H | $-CH_2-CH=C(Cl)-CH_3$ |
| $C_2H_5$ | $CH_3$ | H | H | H | H | $-CH_2-CH_2-CH=CH_2$ |
| $C_2H_5$ | $CH_3$ | H | H | H | H | $-CH_2-CH(CH_3)-CH=CH_2$ |
| $C_2H_5$ | $CH_3$ | H | H | H | H | $-CH_3$ |
| $C_2H_5$ | $CH_3$ | H | H | H | H | $-C_2H_5$ |
| $C_2H_5$ | $CH_3$ | H | H | H | H | $-C_3H_7-n$ |
| $C_2H_5$ | $CH_3$ | H | H | H | H | $-C_5H_{11}-n$ |
| $C_2H_5$ | $CH_3$ | H | H | H | H | $-C_6H_{13}-n$ |
| $C_2H_5$ | $CH_3$ | H | H | H | H | $-C_7H_{15}-n$ |

-continued

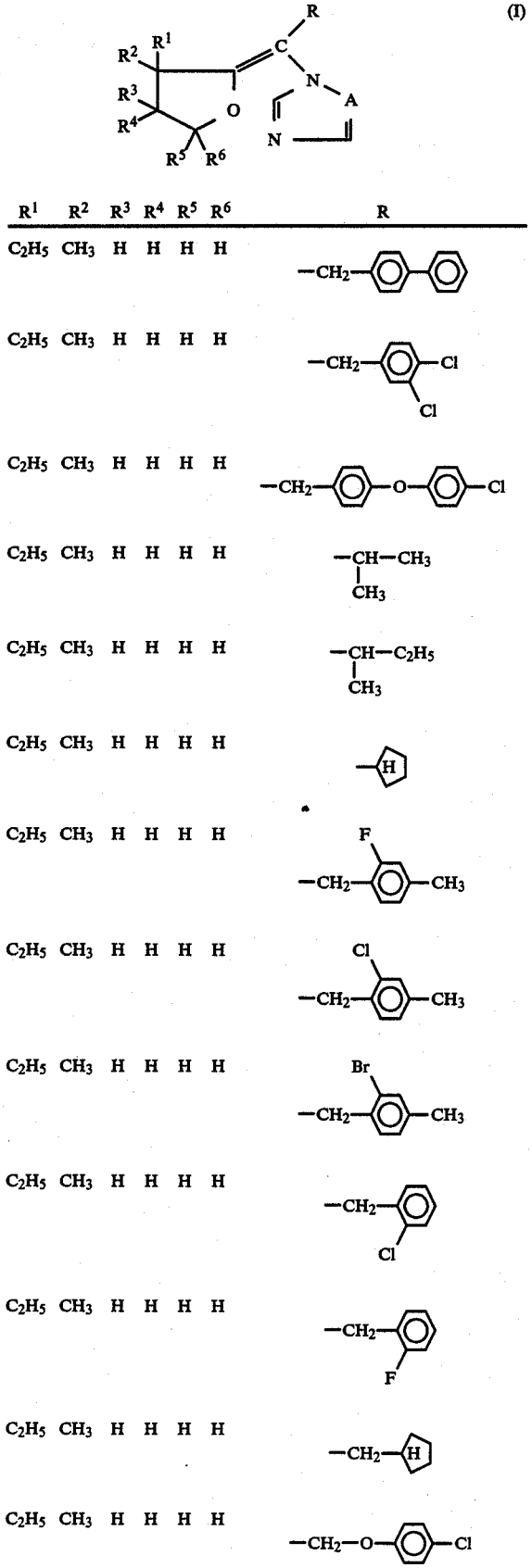

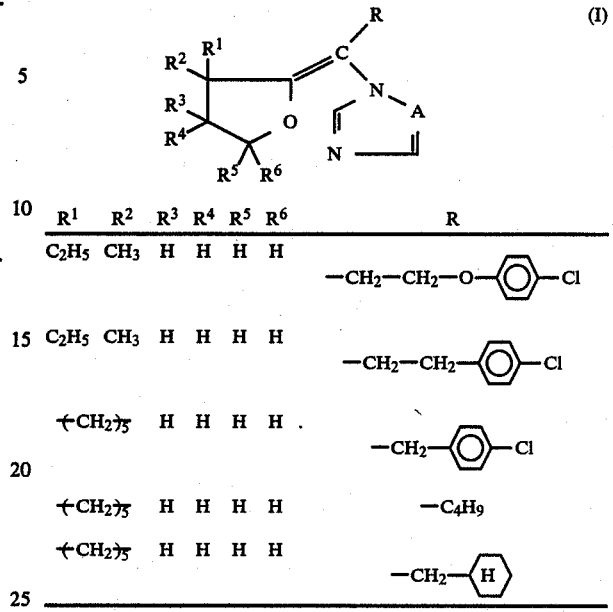

Addition products of acids and those substituted azolyl-tetrahydrofuran-2-ylidene-methane derivatives of the formula (I) in which the substituents A, R and $R^1$ to $R^6$ have the meanings which have already been mentioned as preferred for these substituents are also preferred compounds according to the invention.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Addition products of salts of metals of main groups II to IV and of sub-groups I and II to IV to VIII and those substituted azolyl-tetrahydrofuran-2-ylidenemethane derivatives of the formula (I) in which the substituents A, R and $R^1$ to $R^6$ have the meanings which have already been mentioned as preferred for these substituents are also preferred compounds according to the invention.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, nitric acid and sulphuric acid.

If, for example, 1-(4-chlorophenyl)-2-(3,3-dimethyl-2-hydroxy-tetrahydrofuran-2-yl)-2-(1,2,4-triazol-1-yl)-ethane is used as the starting substance, the course of the reaction in the process according to the invention can be represented by the following equation:

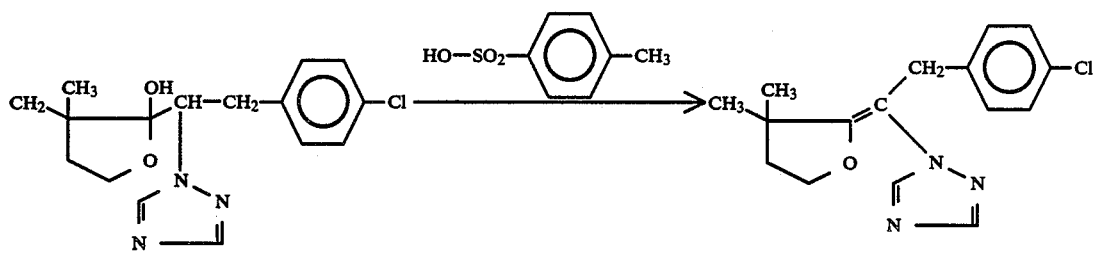

Formula (II) provides a general definition of the azolyl-(2-hydroxytetrahydrofuran-2-yl)-methane derivatives to be used as starting substances in carrying out the process according to the invention. In this formula, A, R and $R^1$ to $R^6$ preferably represent the radicals which have already been mentioned as preferred for these substituents in connection with the description of the substances of the formula (I) according to the invention.

The azolyl-(2-hydroxy-tetrahydrofuran-2-yl)methane derivatives of the formula (II) are not yet known; they are obtained by a process in which (a) 2-azolylmethyl-2-hydroxy-tetrahydrofurans of the formula

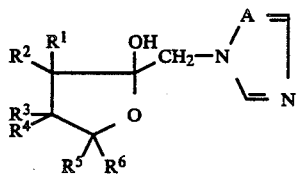

(III)

in which

A and $R^1$ to $R^6$ have the abovementioned meaning, are reacted with an alkylating agent of the formula (IV)

Z—R (IV)

in which

R has the abovementioned meaning and

Z represents an electron-withdrawing leaving grouping, such as, for example, p-methylphenylsulphonyloxy, the grouping —O—SO$_2$—OR' or —NR$_3$' or the like, wherein R' represents, for example, an optionally substituted hydrocarbon radical, in the presence of a diluent and in the presence of a base.

Possible diluents for process (a) are inert organic solvents. The include, preferably, aromatic hydrocarbons, such as benzene, toluene or xylene; halogenated hydrocarbons, such as methylene chloride, carbon tetrachloride, chloroform or chlorobenzene; esters, such as ethyl acetate; formamides, such as dimethylformamide; and dimethylsulphoxide.

Process (a) is carried out in the presence of a base. All the customary organic and, in particular, inorganic bases can be used here, such as, preferably, alkali metal hydroxides or alkali metal carbonates, sodium hydroxide and potassium hydroxide being mentioned as examples.

The reaction temperatures can be varied within a substantial range in carrying out process (a). In general, the reaction is carried out between 0° and 100° C., preferably between 20° and 100° C.

In carrying out process (a), 1 to 1.2 moles of alkylating agent are preferably employed per mole of the compound of the formula (III). The intermediates of the formula (II) are isolated in a generally customary manner.

Process (a) can also be carried out in a two-phase system, such as, for example, aqueous sodium hydroxide solution or potassium hydroxide solution/toluene or methylene chloride, if appropriate with addition of 0.1 to 1 mole of a phase transfer catalyst, such as, for example, ammonium or phosphonium compounds, examples which may be mentioned being benzyldodecyldimethyl-ammonium chloride and triethyl-benzyl-ammonium chloride.

The 2-azolylmethyl-2-hydroxy-tetrahydrofurans of the formula (III) to be used as starting substances for process (a) are likewise not yet known; they are obtained by a process in which (b) water is added onto 2-azolylmethylene-tetrahydrofurans of the formula (V)

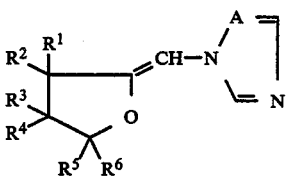

(V)

in which

A and $R^1$ to $R^6$ have the abovementioned meaning, in the presence of a diluent and in the presence of an acid as a catalyst.

Possible diluents for process (b) are water-miscible solvents. These include, preferably, alcohols, such as methanol or ethanol; ketones, such as acetone; and water.

Process (b) is carried out in the presence of an acid as a catalyst. All the customary organic and inorganic acids can be employed here, such as, preferably, sulphuric acid, hydrochloric acid, nitric acid, methanesulphonic acid and p-toluenesulphonic acid.

The reaction temperatures can be varied within a substantial range in carrying out process (b). In general, the reaction is carried out between 0° and 100° C., preferably between 20° and 80° C.

The alkylating agents of the formula (IV) also to be used as starting substances for process (a) are generally known compounds of organic chemistry.

Some of the 2-azolylmethylene-tetrahydrofurans of the formula (V) to be used as starting substances for process (b) are known U.S. Pat. No. 4,487,776, corresponding to German Published Specification No.

3,204,795). The 2-azolylmethylene-tetrahydrofurans of the formula (Va) are not yet known.

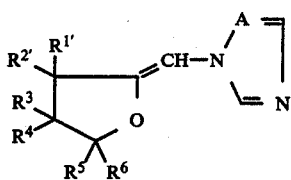
(Va)

in which

A and $R^3$ to $R^6$ have the abovementioned meaning and $R^{1'}$ and $R^{2'}$ represent the abovementioned meanings of $R^1$ and, respectively, $R^2$, the two radicals not simultaneously representing methyl if $R^3$ to $R^6$ simultaneously represent hydrogen.

The 2-azolylmethylene-tetrahydrofurans of the formula (V) or (Va) are obtained by a process in which (c) halogenoketones of the formula (VI)

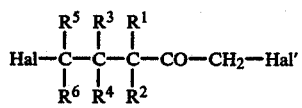
(VI)

in which $R^1$ to $R^6$ have the abovementioned meaning and

Hal and Hal' represent halogen, preferably chlorine or bromine, are reacted with azoles of the formula (VII)

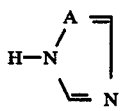
(VII)

in which

A has the abovementioned meaning, in the presence of a diluent and in the presence of an acid-binding agent.

Possible diluents for process (c) are inert organic solvents. These include, preferably, ketones, such as diethyl ketone and, in particular, acetone and methyl ethyl ketone; nitriles, such as propionitrile, in particular acetonitrile; alcohols, such as ethanol or isopropanol; ethers, such as tetrahydrofuran or dioxane; aromatic hydrocarbons, such as toluene, benzene or chlorobenzene; formamides, such as, in particular, dimethylformamide; and halogenated hydrocarbons.

Process (c) is carried out in the presence of an acid-binding agent. All the inorganic or organic acid-binding agents which can customarily be used may be added, such as alkali metal carbonates, for example sodium carbonate, potassium carbonate and sodium bicarbonate, or such as lower tertiary alkylamines, cycloalkylamines or aralkylamines, for example triethylamine, N,N-dimethylcyclohexylamine, dicyclohexylamine and N,N-dimethylbenzylamine, and furthermore pyridine and diazabicyclooctane.

An appropriate excess of azole is preferably used.

The reaction temperatures can be varied within a substantial range in carrying out process (c). In general, the reaction is carried out between about 20° and 150° C., preferably at 60° to 120° C.

In carrying out process (c), 1 to 4 moles of azole of the formula (VII) and 1 to 4 moles of acid-binding agent are preferably employed per mole of the compounds of the formula (VI). The compounds of the formula (V) or (Va) are isolated in the customary manner.

Some of the halogenoketones of the formula (VI) to be used as starting substances for process (c) are known U.S. Pat. No. 4,507,496 corresponding to German Published Specification No. 3,204,788). The halogenoketones of the formula (VIa)

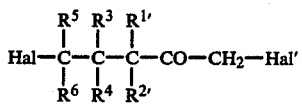
(VIa)

in which

Hal, Hal', $R^3$ to $R^6$, $R^{1'}$ and $R^{2'}$ have the abovementioned meaning, are not yet known.

The halogenoketones of the formula (VI) or (VIa) are obtained by a process in which (d) 2-chloromethylene-tetrahydrofurans of the formula (VIII)

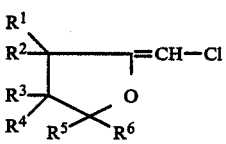
(VIII)

in which $R^1$ to $R^6$ have the abovementioned meaning, are reacted with acid compounds of the formula (IX)

H—Hal (IX)

in which

Hal has the abovementioned meaning, if appropriate in the presence of a diluent.

Possible diluents for process (d) are inert organic solvents. These include, preferably, aromatic hydrocarbons, such as toluene, benzene or chlorobenzene; formamides, such as dimethylformamide; nitriles, such as acetonitrile; and halogenated hydrocarbons, such as methylene chloride.

The reaction temperatures can be varied within a substantial range in carrying out process (d). In general, the reaction is carried out between 0° and 150° C.; preferably at 10° to 120° C.

Certain halogenoketones of the formula (VI) or (VIa) can also be obtained by reacting correspondingly substituted ketones or unsaturated ketones with halogenating agents, such as, for example, bromine, hydrogen bromide or sulphuryl chloride, in the customary manner (in this context, compare also the preparation examples).

The azoles of the formula (VII) also to be used as starting substances for process (c) are generally known compounds of organic chemistry.

Some of the 2-chloromethylene-tetrahydrofurans of the formula (VIII) to be used as starting substances for process (d) are known (compare DE-OS (German Published Specification), No. 3,204,692). The 2-chloromethylene-tetrahydrofurans of the formula (VIIIa)

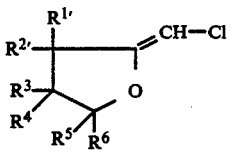

in which

R$^{1\prime}$, R$^{2\prime}$ and R$^3$ to R$^6$ have the abovementioned meaning, are not yet known.

The 2-chloromethylene-tetrahydrofurans of the formula (VIII) or (VIIIa) are obtained by a process in which, for example, (e) 1,1,5-trichloro-pentene derivatives of the formula (X)

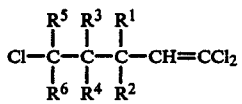

in which

R$^1$ to R$^6$ have the abovementioned meaning, or 1,1,1,5-tetrachloro-pentane derivatives of the formula (XI)

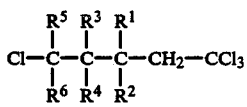

in which

R$^1$ to R$^6$ have the abovementioned meaning, are reacted with carboxylates, such as, in particular, anhydrous sodium acetate, and with bases, such as, in particular, alkali metal alcoholates, in the presence of a diluent.

Possible diluents for process (e) are inert organic solvents. These include, preferably, formamides, such as dimethylformamide; nitriles, such as acetonitrile; and halogenated hydrocarbons.

The reaction temperatures can be varied within a substantial range in carrying out process (e). In general, the reaction is carried out between 20° and 150° C., preferably at the boiling point of the solvent used.

In carrying out process (e), 1 to 2 moles of carboxylate and 1 to 2 moles of base are preferably employed per mole of the compounds of the formulae (X) or (XI). The desired products are isolated in the customary manner.

The acid compounds of the formula (IX) to be used as starting substances for process (d) according to the invention are generally known compounds of organic chemistry.

The compounds of the formula (X) or (XI) to be used as starting substances for process (e) are known compounds of organic chemistry, or they can be obtained in a known manner.

Possible diluents for the reaction according to the invention are inert organic solvents. These include, preferably, aromatic hydrocarbons, such as toluene, benzene, xylene, chlorobenzene or dichlorobenzene; and halogenated aliphatic hydrocarbons, such as dichloroethane.

The reaction according to the invention is carried out in the presence of an acid catalyst. Acid catalysts include, preferably, aliphatic and aromatic sulphonic acids, such as p-toluenesulphonic acid or methanesulphonic acid, which may also optionally be in polymer-bonded form.

The reaction temperatures can be varied within a substantial range in the reaction according to the invention. In general, the reaction is carried out between about 50° and 150° C., preferably at 80° to 120° C.

In carrying out the reaction according to the invention, catalytic amounts of acid catalyst are employed per mole of the compounds of the formula (II). The compounds of the formula (I) are isolated in the customary manner.

The acid addition salts of the compounds of the formula (I) can be obtained in a simple manner by customary salt formation methods, for example by dissolving a compound of the formula (I) in a suitable inert solvent and adding the acid, for example hydrochloric acid, and, if appropriate, purified by washing with an organic solvent.

The metal salt complexes of the compounds of the formula (I) can be obtained in a simple manner by customary processes, thus, for example, by dissolving the metal salt in alcohol, for example ethanol, and adding the solution to the compounds of the formula (I). The metal salt complexes can be purified in a known manner, for example by filtration.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Sphaerotheca species, such as against the powdery mildew of barley causative organism (Sphaerotheca fuliginea); Botrytis species, such as against the grey mould causative organism (*Botrytis cinerea*); cereal diseases, such as *Erysiphe graminis*, rusts, Septoria, *Cochliobolus sativus*, *Pyrenophora teres* or *Pyrenophora graminea;* and rice diseases, such as *Pyricularia oryzae* and *Pellicularia sasakii*. The substances according to the invention also exhibit a broad and good in vitro fungicidal action spectrum.

It should be emphasized that the substances according to the invention not only have a protective action but in some cases are also systemic. Thus, it is possible to protect plants from fungal attack if the active compound is fed to the above-ground parts of the plant via the soil and the root or via the seed.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compounds, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenbenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifies, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesive such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipds, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

EXAMPLE 1 and 2

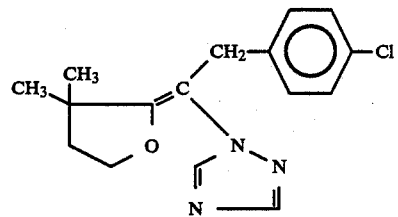

Example (I-1) = form A
Example (I-2) = form B
(Form A and form B =
the two possible geometric isomers)

5 g (0.0155 mole) of 1-(4-chlorophenyl)-2-(3,3-dimethyl-2-hydroxy-tetrahydrofuran-2-yl)-2-(1,2,4-triazol-1-yl)-ethane are dissolved in 100 ml of toluene, 0.5 g of p-toluenesulphonic acid are added and the mixture is heated under reflux for 2 hours, using a water separator. The reaction mixture is cooled, washed with water, dried over sodium sulphate and concentrated in vacuo. The residue is purified by column chromatography (silica gel; ethyl acetate/cyclohexane=3:1). 2.8 g (59.6% of theory) of 1-(4-chlorophenyl-2-(3,3-dimethyl-tetrahydrofuran-2-ylidene)-2-(1,2,4-triazol-1-yl)-ethane are obtained as form A of melting point 89° C. and 0.4 g (8.5% of theory) of 1-(4-chlorophenyl)-2-(3,3-dimethyl-tetrahydrofuran-2-ylidene)-2-(1,2,4-triazol-1-yl)-ethane are obtained as form B of melting point 175°–177° C.

PREPARATION OF THE STARTING SUBSTANCE

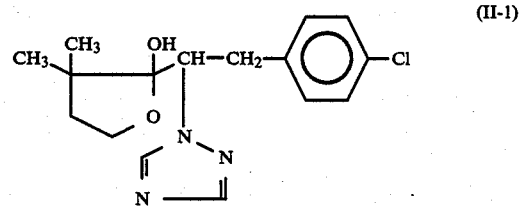

10.3 g (0.052 mole) of 3,3-dimethyl-2-hydroxy-2-(1,2,4-triazol-1-yl-methyl)-tetrahydrofuran, 2.9 g (0.052 mole) of potassium hydroxide and 8.4 g (0.052 mole) of 4-chlorobenzyl chloride are stirred in a mixture of 100 ml of dimethylsulphoxide and 6 ml of water at 30° C. for 2 hours. The reaction solution is then poured onto water and extracted with ethyl acetate. The organic phase is dried over sodium sulphate and concentrated. After trituration in n-hexane, the residue crystallizes. 6.6 g (39.5% of theory) of 1-(4-chlorophenyl)-2-(3,3-dimethyl-2-hydroxy-tetrahydrofuran-2-yl)-2-(1,2,4-triazol-1-yl)ethane of melting point 98° C. are obtained.

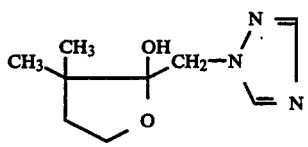
(III-1)

30 g (0.17 mole) of (3,3-dimethyl-tetrahydrofuran-2-ylidene)-(1,2,4-triazol-1-yl)-methane and 100 g of concentrated hydrochloric acid are stirred in 300 ml of methanol at room temperature for 4 hours. The reaction mixture is concentrated in vacuo, the residue is taken up in water, the pH value is adjusted to 7 to 8 with dilute sodium hydroxide solution and the mixture is extracted with methylene chloride. The organic phase is washed with water, dried over sodium sulphate and concentrated in vacuo. 30.7 g (93% of theory) of 3,3-dimethyl-2-hydroxy-2-(1,2,4-triazol-1-yl-methyl)-tetrahydrofuran of melting point 93°–95° C. are obtained.

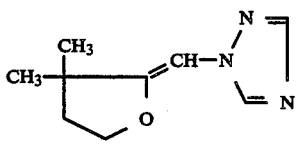
(V-1)

85 g (1.23 moles) of 1,2,4-triazole and 464 g (33.6 moles) of potassium carbonate are initially introduced into 2.5 liters of acetone. 220 g (1.12 moles) of 1,5-dichloro-3,3-dimethyl-2-pentanone are added dropwise at room temperature, without cooling and with stirring. When the addition has ended, the mixture is subsequently stirred at the reflux temperature for 2 hours.

The reaction mixture is cooled and filtered over a suction filter and the mother liquor is concentrated in vacuo. The residue is taken up in methylene chloride and the mixture is washed with water, dried over sodium sulphate and concentrated. The residue is stirred in petroleum ether, filtered off with suction and dried at 50° C. in vacuo. 145.3 g (56.5% of theory) of (3,3-dimethyl-tetrahydro-2-ylidene)-(1,2,4-triazol-1-yl)-methane of melting point 47° C. are obtained.

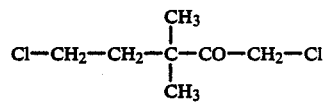
(VI-1)

A powerful stream of hydrogen chloride gas from a cylinder is passed into 476 g (3.25 moles) of 2-chloromethylene-3,3-dimethyltetrahydrofuran, with ice-cooling. The gas is absorbed completely and the internal temperature rises up to 30° C. After complete saturation with hydrogen chloride, the reaction mixture is subsequently stirred at room temperature for 2 hours. Excess hydrogen chloride is initially stripped off using a water pump, and the mixture is then distilled under a high vacuum. 531 g (90% of theory) of 1,5-dichloro-3,3-dimethyl-2-pentanone of boiling point 85°–90° C./0.3 mbar are obtained.

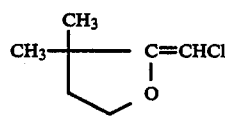
(VIII-1)

806 g (4 moles) of 1,1,5-trichloro-3,3-dimethyl-1-pentene are heated under reflux with 360 g (4.4 moles) of anhydrous sodium acetate in 1 liter of dimethylformamide for 6 hours. After cooling to about 100° C., 1.6 liters (8 moles) of 30% strength sodium methylate solution in methanol are added dropwise and the mixture is heated under reflux for a further 4 hours. The cold solution is poured into water and extracted several times with methylene chloride. After the solution has been dried and the solvent has been distilled off, 654 g of product remain, and are fractionated over a column. 522 g (80% of theory) of 2-chloromethylene-3,3-dimethyl-tetrahydrofuran of boiling point 84°–87° C./20 mbar are obtained.

The following end products of the general formula

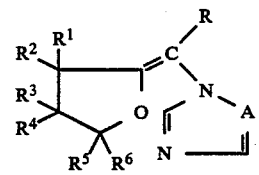
(I)

are obtained in a corresponding manner according to the process conditions described:

| Example No. | R¹ | R² | R³ | R⁴ | R⁵ | R⁶ | R | A | m.p. (°C.) or $n_D^{20}$ |
|---|---|---|---|---|---|---|---|---|---|
| I-3 | C₂H₅ | CH₃ | H | H | H | H |  | N | 1.5607 (Form A) |
| I-4 | C₂H₅ | CH₃ | H | H | H | H | 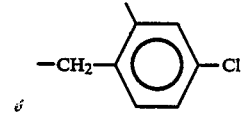 | N | 78 (Form B) |

-continued

| Example No. | $R^1$ | $R^2$ | $R^3$ | $R^4$ | $R^5$ | $R^6$ | R | A | m.p. (°C.) or $n_D^{20}$ |
|---|---|---|---|---|---|---|---|---|---|
| I-5 | $CH_3$ | $CH_3$ | H | H | H | H | -CH$_2$-(2,4-Cl$_2$C$_6$H$_3$) | N | 69–70 (Form A) |
| I-6 | $CH_3$ | $CH_3$ | H | H | H | H | -CH$_2$-(2,4-Cl$_2$C$_6$H$_3$) | N | 106 (Form B) |
| I-7 | $CH_3$ | $CH_3$ | H | H | H | H | —C$_4$H$_9$ | N | 1.4959 (Form A) |
| I-8 | $CH_3$ | $CH_3$ | H | H | H | H | -CH$_2$-cyclohexyl | N | 1.5158 (Form A) |
| I-9 | $CH_3$ | $CH_3$ | H | H | H | H | -CH$_2$-cyclohexyl | N | 118 |
| I-10 | $CH_3$ | $CH_3$ | H | H | H | H | -CH$_2$-(4-ClC$_6$H$_4$) | CH | 1.5616 |
| I-11 | $CH_3$ | $CH_3$ | H | H | H | H | -CH$_2$-(2,4-Cl$_2$C$_6$H$_3$) | CH | 1.5672 |
| I-12 | $CH_3$ | $CH_3$ | H | H | H | H | -CH$_2$-(4-FC$_6$H$_4$) | CH | 1.5429 |
| I-13 | $CH_3$ | $CH_3$ | H | H | H | H | -CH$_2$-C$_6$H$_5$ | CH | 1.5530 |
| I-14 | $CH_3$ | $CH_3$ | H | H | H | H | —C$_4$H$_9$ | CH | 1.5016 |
| I-15 | $CH_3$ | $CH_3$ | H | H | H | H | —CH$_2$—CH=CH$_2$ | CH | 1.5163 |
| I-16 | $C_2H_5$ | $CH_3$ | H | H | H | H | -CH$_2$-(4-ClC$_6$H$_4$) | N | 70–75 (Form A) |
| I-17 | $C_2H_5$ | $CH_3$ | H | H | H | H | -CH$_2$-(4-ClC$_6$H$_4$) | N | 60–65 |
| I-18 | $C_2H_5$ | $CH_3$ | H | H | H | H | -CH$_2$-(4-ClC$_6$H$_4$) | CH | 1.5574 |

-continued

| Example No. | R¹ | R² | R³ | R⁴ | R⁵ | R⁶ | R | A | m.p. (°C.) or $n_D^{20}$ |
|---|---|---|---|---|---|---|---|---|---|
| I-19 | $C_2H_5$ | $CH_3$ | H | H | H | H | $-CH_2-\text{C}_6\text{H}_4-F$ | CH | 1,5441 |
| I-20 | $CH_3$ | $C_2H_5$ | H | H | H | H | $-CH_2-\text{C}_6\text{H}_4-Br$ | CH | 1,5726 |
| I-21 | $CH_3$ | $CH_3$ | H | H | H | H | $-CH_2-\text{C}_6\text{H}_3(Cl)(F)$ | N | 1,5471 |

Form A and Form B = the two possible geometric isomers

The following starting substances of the formula (II)

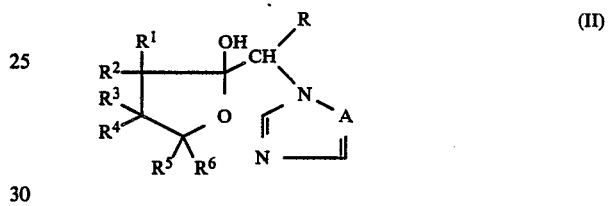

can be obtained according to Example 1 and the process conditions described:

| Example NO. | R¹ | R² | R³ | R⁴ | R⁵ | R⁶ | R | A | m.p. (°C.) or $n_D^{20}$ |
|---|---|---|---|---|---|---|---|---|---|
| II-2 | $CH_3$ | $CH_3$ | H | H | H | H | $-C_4H_9$ | N | 1.4888 |
| II-3 | $CH_3$ | $CH_3$ | H | H | H | H | $-CH_2-\text{C}_6H_{11}$ | N | 109 |
| II-4 | $CH_3$ | $CH_3$ | H | H | H | H | $-CH_2-\text{C}_6H_3(Cl)(Cl)$ | N | 123-25 |
| II-5 | $C_2H_5$ | $CH_3$ | H | H | H | H | $-CH_2-\text{C}_6H_4-Cl$ | N | 1.5349 |
| II-6 | $C_2H_5$ | $CH_3$ | H | H | H | H | $-CH_2-\text{C}_6H_3(Cl)(Cl)$ | N | 1.5368 |
| II-7 | $CH_3$ | $CH_3$ | H | H | H | H | $-CH_2-\text{C}_6H_4-Cl$ | CH | 130-32 |
| II-8 | $CH_3$ | $CH_3$ | H | H | H | H | $-C_4H_9$ | CH | 1.4913 |

-continued

| Example NO. | $R^1$ | $R^2$ | $R^3$ | $R^4$ | $R^5$ | $R^6$ | R | A | m.p. (°C.) or $n_D^{20}$ |
|---|---|---|---|---|---|---|---|---|---|
| II-9 | $CH_3$ | $CH_3$ | H | H | H | H | -CH$_2$-(2,4-dichlorophenyl) | CH | 164 |
| II-10 | $CH_3$ | $CH_3$ | H | H | H | H | -CH$_2$-(4-fluorophenyl) | CH | 144–45 |
| II-11 | $CH_3$ | $CH_3$ | H | H | H | H | $-CH_2-CH=CH_2$ | CH | 1.5065 |
| II-12 | $CH_3$ | $CH_3$ | H | H | H | H | -CH$_2$-phenyl | CH | 135–36 |

The following starting substances of the formula (III)

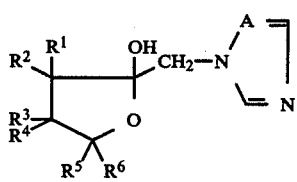

(III)

can be obtained according to Example 1 and the process conditions described:

| Example No. | $R^1$ | $R^2$ | $R^3$ | $R^4$ | $R^5$ | $R^6$ | A | m.p. (°C.) |
|---|---|---|---|---|---|---|---|---|
| III-2 | $C_2H_5$ | $CH_3$ | H | H | H | H | N | 88 |
| III-3 | $CH_3$ | $CH_3$ | H | H | H | H | CH | 107–08 |

The following starting substances of the formula (Va)

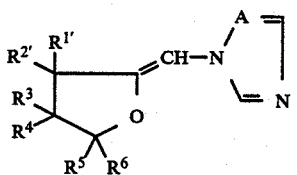

(Va)

can be obtained according to Example 1 and the process conditions described:

| Example No. | $R^{1'}$ | $R^{2'}$ | $R^3$ | $R^4$ | $R^5$ | $R^6$ | A | $n_D^{20}$ |
|---|---|---|---|---|---|---|---|---|
| Va-1 | $CH_3$ | $CH_3$ | H | H | $CH_3$ | H | N | 1.5219 |
| Va-2 | $C_2H_5$ | $CH_3$ | H | H | H | H | N | 1.5237 |
| Va-3 | $CH_3$ | $CH_3$ | H | H | $-CH_2Br$ | H | N | 1.5452 |
| Va-4 | $C_2H_5$ | $CH_3$ | H | H | H | H | CH | 1.5364 |

The following examples demonstrate further possibilities of the preparation of starting substances of the formula (VI) or (VIa):

EXAMPLE A

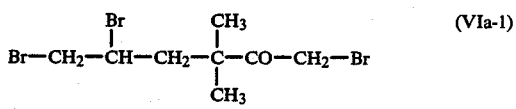

(VIa-1)

170.7 g (1.066 moles) of bromine are added dropwise to 67.2 g (0.533 mole) of 3,3-dimethyl-5-hexen-2-one in 500 ml of chloroform at room temperature. The mixture is subseqently stirred for 30 minutes, washed with water, dried over sodium sulphate and concentrated in vacuo. 188 g (96.5% of theory) of 3,3-dimethyl-1,5,6-tribromo-2-hexanone of refractive index $n_D^{20}=1.5387$ are obtained.

EXAMPLE B

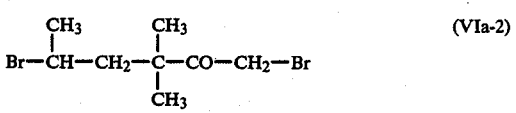

(VIa-2)

20.9 g (0.13 mole) of bromine are added dropwise to 27 g (0.13 mole) of 5-bromo-3,3-dimethyl-2-hexanone in 50 ml of chloroform at room temperature. The mixture is subsequently stirred at room temperature for 30 minutes, washed with water, dried over sodium sulphate and concentrated in vacuo. 36.9 g (99% of theory) of 1,5-dibromo-3,3-dimethyl-2-hexanone of refractive index $n_D^{20}=1.5015$ are obtained.

PREPARATION OF THE INTERMEDIATE

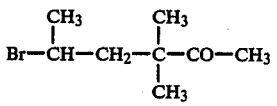

18.9 g (0.15 mole) of 3,3-dimethyl-5-hexen-2-one and 1.6 g (0.0054 mole) of iron-III bromide are dissolved in 150 ml of chloroform. 0.16 mole of hydrogen bromide gas are passed in at 0° C. in the course of 90 minutes. The mixture is subsequently stirred at room temperature for 2 hours and the organic phase is separated off, washed with water, dried over sodium sulphate and concentrated in vacuo. 27 g (87% of theory) of 5-bromo-3,3-dimethyl-2-hexanone of refractive index $n_D^{20}=1.4639$ are obtained.

USE EXAMPLES

The compounds shown below are used as comparison substances in the use examples which follow:

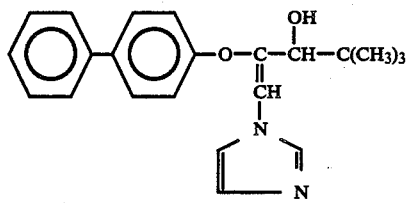 (A)

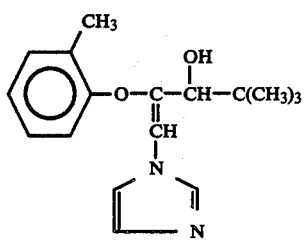 (B)

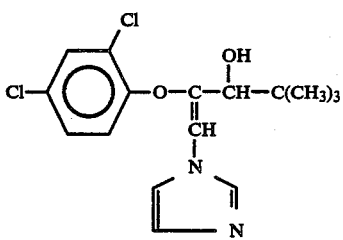 (C)

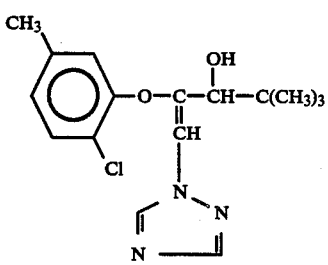 (D)

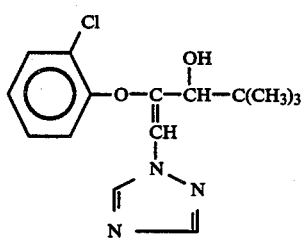 (F)

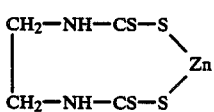 (F)

EXAMPLE A

Botrytis test (bean)/protective

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small pieces of agar covered with *Botrytis cinerea* are placed on each leaf. The inoculated plants are placed in a darkened humidity chamber at 20° C. 3 days after the inoculation, the size of the infected spots on the leaves is evaluated.

In this test, a clearly superior activity compared with the prior art is shown, for example, by the compounds according to preparation examples: 1, 6, 10, 16 and 17.

EXAMPLE B

Sphaerotheca test (cucumber)/protective

Solvent: 4.7 parts by weight of acetone
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to preparation examples: 5 and 6.

EXAMPLE C

Pyricularia test (rice)/protective

Solvent: 12.5 parts by weight of acetone
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation examples: 1, 9, 12 and 11.

EXAMPLE D

Pyricularia test (rice)/systemic

Solvent: 12.5 parts by weight of acetone
Emulsifier: 0.3 parts by weight of alkylaryl polyglycol ether.

To produce a suitable preparation of active compound, 1 part by weight of active compound is mixed with the stated amounts of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to preparation examples: 1, 9, 14 and 12.

EXAMPLE E

Pellicularia test (rice)

Solvent: 12.5 parts by weight of acetone
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for activity, young rice plants in the 3 to 4 leaf stage are sprayed until dripping wet. The plants remain in a greenhouse until they have dried off. The plants are then inoculated with *Pellicularia sasakii* and are placed at 25° C. and 100% relative atmospheric humidity.

The evaluation of the disease infestation is carried out 5 to 8 days after the inoculation.

In this test, a clearly superior activity compared with the prior art is shown, for example, by the compounds according to preparation examples: 1, 9, 14, 12 and 11.

EXAMPLE F

Erysiphe test (barley)/protective

Solvent: 100 parts by weight of dimethylformamide
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f.sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to preparation examples: 1, 5, 10, 11 and 12.

EXAMPLE G

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes. 3 batches of 12 grains of the barley are sown 2 cm deep in standard soil. 7 days after sowing, when the young plants have unfolded their first leaf, they are dusted with spores of *Erysiphe graminis* f.sp. hordei.

The plants are placed in a greenhouse at a temperature of about 20° C. and a relative atmospheric humidity of about 80% in order to promote the development of powdery mildew pustules.

Evaluation is carried out 7 days after the inoculation.

In this test, a clearly superior activity compared with the prior art is shown, for example, by the compound according to preparation example: 1.

EXAMPLE H

*Drechslera graminea* test (barley)/seed treatment (syn. *Helminthosporium gramineum*)

The active compounds are used as dry dressings. These are prepared by extending the particular active compound with a ground mineral to give a finely pulverulent mixture, which ensures uniform distribution on the seed surface.

To apply the dressing, the infected seed is shaken with the dressing in a closed glass flask for 3 minutes.

The seed is embedded in sieved, moist standard soil and is exposed to a temperature of 4° C. in closed Petri dishes in a refrigerator for 10 days. Germination of the barley, and possibly also of the fungus spores, is thereby initiated. 2 batches of 50 grains of the pregerminated barley are subsequently sown 3 cm deep in standard soil and are cultivated in a greenhouse at a temperature of about 18° C., in seedboxes which are exposed to light for 15 hours daily.

About 3 weeks after sowing, the plants are evaluated for symptoms of stripe disease.

In this test, a clearly superior activity compared with the prior art is shown, for example, by the compounds according to preparation examples: 14 and 10.

It will be understood that the specification and examples are illustrative but not limitative of the present invention and that other embodiments within the spirit and scope of the invention will suggest themselves to those skilled in the art.

We claim:

1. An azolyl-(2-hydroxytetrahydrofuran-2-yl)-methane derivative of the formula

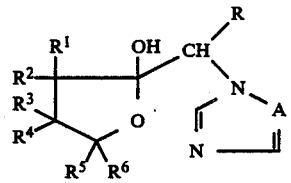

in which

A represents a nitrogen atom or the CH group,

R represents straight-chain or branched alkyl with 1 to 12 carbon atoms, or represents straight-chain or branched alkenyl or alkynyl with in each case 2 to 12 carbon atoms, or represents straight-chain or branched alkoxyalkyl or alkylthioalkyl with in each case 1 to 6 carbon atoms in each alkyl part, or represents halogenoalkyl, halogenoalkoxyalkyl or halogenoalkylthioalkyl with in each case 1 to 6 carbon atoms in each alkyl part and with in each case 1 to 6 identical or different halogen atoms or represents halogenoalkyl with 2 to 6 carbon atoms and 1 to 5 identical or different halogen atoms, or represents phenylalkyl, phenoxyalkyl or phenylthioalkyl with in each case 1 to 4 carbon atoms in the alkyl part and in each case optionally monosubstituted or polysubstituted in the phenyl part by identical or different substituents selected from the group consisting of halogen, alkyl, alkoxy and alkylthio with in each case 1 to 4 carbon atoms; halogenoalkyl, halogenoalkoxy and halogenoalkylthio with in each case 1 to 4 carbon atoms and 1 to 5 identical or different halogen atoms; nitro; cyano; and optionally halogen-substituted phenyl and phenoxy; or represents cycloalkyl or cycloalkylalkyl with in each case 3 to 7 carbon atoms in the cycloalkyl part and 1 to 4 carbon atoms in the alkyl part and in each case optionally monosubstituted or polysubstituted by alkyl with 1 to 4 carbon atoms;

$R^1$ to $R^6$, which can be identical or different, represent hydrogen, straight-chain or branched alkyl with 1 to 4 carbon atoms, or represent halogenoalkyl with 1 or 2 carbon atoms and 1 to 5 identical or different halogen atoms, up to a maximum of 3 substituents representing halogenoalkyl, $R^3$ to $R^6$, which can be identical or different, also represent halogen, up to a maximum of 3 substituents having this meaning; or $R^1$ and $R^2$, together with the carbon atom to which they are bonded, represent cycloalkyl which has 4 to 7 carbon atoms and is optionally substituted by alkyl with 1 or 2 carbon atoms; or $R^2$ and $R^3$, together with the carbon atoms to which they are bonded, represent cycloalkyl which has 4 to 7 carbon atoms and is optionally substituted by alkyl with 1 or 2 carbon atoms.

2. A compound according to claim 1, in which

R represents straight-chain or branched alkyl with 1 to 8 carbon atoms, or represents straight-chain or branched alkenyl or alkynyl with in each case 2 to 6 carbon atoms, or represents straight-chain or branched alkoxyalkyl or alkylthioalkyl with in each case 1 to 4 carbon atoms in each alkyl part, or represents halogenalkyl, halogenoalkoxyalkyl or halogenoalkylthioalkyl with in each case 1 to 4 carbon atoms in each alkyl part and with in each case 1 to 5 fluorine and/or chlorine atoms, or represents halogenoalkenyl with 2 to 4 carbon atoms and 1 to 3 fluorine and/or chlorine atoms; or represents phenylalkyl, phenoxyalkyl or phenylthioalkyl with in each case 1 or 2 carbon atoms in the alkyl part and in each case optionally mono-, di- or tri-substituted in the phenyl part by identical or different substituents selected from the group consisting of fluorine, chlorine, methyl, ethyl, isopropyl, tert.-butyl, methoxy, methylthio, trifluoromethyl, trifluoromethoxy, trifluoromethylthio, nitro, cyano and optionally chlorine-substituted phenyl and phenoxy; or represents cyclohexyl or cyclohexylmethyl, in each case optionally substituted by methyl and/or ethyl;

$R^1$ to $R^6$, which can be identical or different, represent hydrogen, methyl, ethyl or halogenomethyl with 1 to 3 identical or different halogen atoms, a maximum of three substituents representing halogenomethyl; or $R^3$ to $R^6$, which can be identical or different, also represent fluorine, chlorine or bromine, up to a maximum of three substituents having this meaning; or $R^1$ and $R^2$, together with the carbon atom to which they are bonded, represent cyclopentyl or cyclohexyl; or $R^2$ and $R^3$, together with the carbon atoms to which they are bonded, represent cyclopentyl or cyclohexyl.

3. A compound according to claim 1, in which R is hydrogen.

4. A compound according to claim 1, in which $R^1$ and $R^2$ are alkyl and $R^3$ to $R^6$ are hydrogen.

5. A compound according to claim 1, wherein such compound is 1-(4-chlorophenyl)-2-(3,3-dimethyl-2-hydroxy-tetrahydrofuran-2-yl)-2-(1,2,4-triazol-1-yl)-ethane of the formula

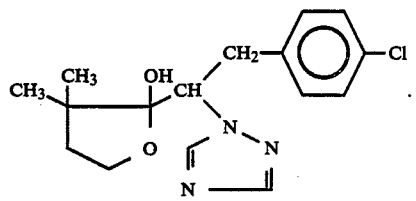

6. A compound according to claim 1, wherein such compound is 1-cyclohexyl-2-(3,3-dimethyl-2-hydroxy-tetrahydrofuran-2-yl)-2-(1,2,4-triazol-1-yl)-ethane of the formula

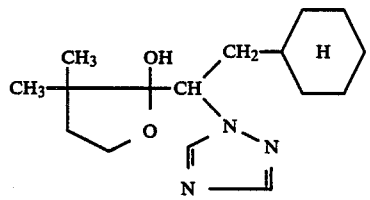

7. A compound according to claim 1, wherein such compound is 1-(4-chlorophenyl)-2-(3,3-dimethyl-2-hydroxy-tetrahydrofuran-2-yl)-2-(imidazol-1-yl)-ethane of the formula

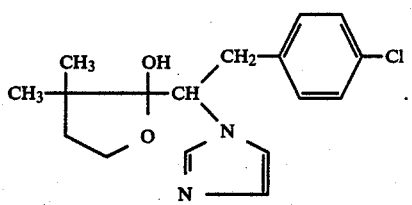

8. A compound according to claim 1, wherein such compound is 1-(2,4-dichlorophenyl)-2-(3,3-dimethyl-2-hydroxy-tetrahydrofuran-2-yl)-2-(imidazole-1-yl)-ethane of the formula

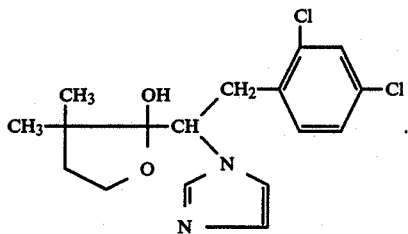

9. A compound according to claim 1, wherein such compound is 1-(4-fluorophenyl)-2-(3,3-dimethyl-2-hydroxy-tetrahydrofuran-2-yl)-2-(imidazol-1-yl)-ethane of the formula

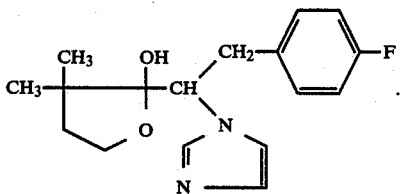

10. A compound according to claim 1, wherein such compound is 1-(3,3-dimethyl-2-hydroxy-tetrahydrofuran-2-yl)-1-(imidazol-1-yl)-pentane of the formula

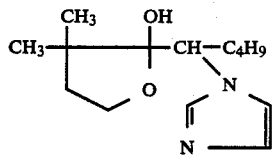

11. A compound according to claim 1, wherein such compound is 1-(4-chlorophenyl)-2-(3-ethyl-3-methyl-2-hydroxy-tetrahydrofuran-2-yl)2-(1,2,4-triazol-1-yl)-ethane of the formula

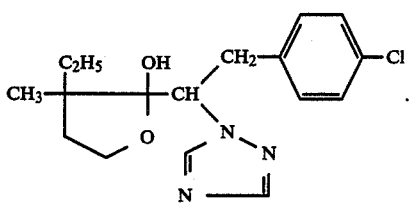

12. A compound according to claim 1, wherein such compound is 3,3-dimethyl-2-hydroxy-2-(1,2,4-triazol-1-yl-methyl)-tetrahydrofuran of the formula

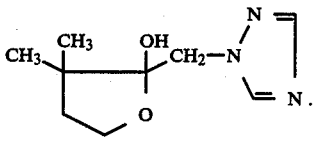

13. A compound according to claim 1, wherein such compound is 3,3-dimethyl-2-hydroxy-2-(imidazol-1-yl-methyl)-tetrahydrofuran of the formula

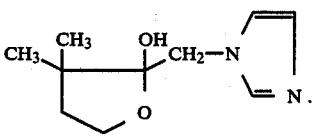

14. A compound according to claim 1, wherein such compound is 3-ethyl-3-methyl-2-hydroxy-2-(1,2,4-triazol-1-yl-methyl)-tetrahydrofuran of the formula

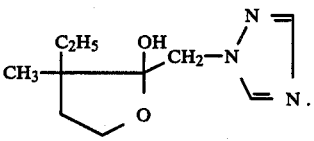

* * * * *

UNITED STATES PATENT AND TRADEMARK OFFICE
CERTIFICATE OF CORRECTION

PATENT NO. : 4,748,249
DATED : May 31, 1988
INVENTOR(S) : Hans-Ludwig Elbe, et al It is certified that error appears in the above-identified patent and that said Letters Patent is hereby corrected as shown below:

| | |
|---|---|
| Col. 9, second formula under column "R" | Delete end of formula and substitute -- -Cl -- |
| Col. 11, line 55 | Delete "The" and substitute --These-- |
| Col. 16, line 36 | Correct --Deuteromycetes-- |
| Col. 17, lines 50-51 | Correct spelling of --phospholipids-- |
| Col. 20, line 1 | Delete "tetrahydro" and substitute --tetrahydrofuran-- |
| Col. 20, line 38 | Delete "80%" and substitute --89%-- |
| Col. 31, line 65 | Correct --halogenoalkyl-- |
| Col. 33, line 16 | Delete "imidazole" and substitute --imidazol-- |

Signed and Sealed this

Twentieth Day of December, 1988

Attest:

DONALD J. QUIGG

*Attesting Officer*     *Commissioner of Patents and Trademarks*